United States Patent
Driessen

(10) Patent No.: US 11,235,019 B2
(45) Date of Patent: Feb. 1, 2022

(54) COMPOSITIONS AND METHODS FOR TREATING TRAVELER'S DIARRHEA

(71) Applicant: ARTESA LLC, Minneapolis, MN (US)

(72) Inventor: William E. Driessen, Minneapolis, MN (US)

(73) Assignee: ARTESA LLC, Minneapolis, MN (US)

( * ) Notice: Subject to any disclaimer, the term of this patent is extended or adjusted under 35 U.S.C. 154(b) by 513 days.

(21) Appl. No.: 15/486,248

(22) Filed: Apr. 12, 2017

(65) Prior Publication Data

US 2018/0296628 A1 Oct. 18, 2018

(51) Int. Cl.
| | | |
|---|---|---|
| *A61K 36/82* | (2006.01) | |
| *A23P 10/28* | (2016.01) | |
| *A23L 33/105* | (2016.01) | |
| *A23L 33/175* | (2016.01) | |
| *A23L 2/52* | (2006.01) | |
| *A61K 31/353* | (2006.01) | |
| *A61K 31/736* | (2006.01) | |
| *A61K 31/198* | (2006.01) | |
| *A61K 9/00* | (2006.01) | |
| *A23F 3/14* | (2006.01) | |
| *A23L 27/30* | (2016.01) | |
| *A23L 33/21* | (2016.01) | |
| *A23L 2/39* | (2006.01) | |
| *A23L 2/60* | (2006.01) | |
| *A23F 3/32* | (2006.01) | |

(52) U.S. Cl.
CPC .............. *A61K 36/82* (2013.01); *A23F 3/14* (2013.01); *A23L 2/52* (2013.01); *A23L 33/105* (2016.08); *A23L 33/175* (2016.08); *A23P 10/28* (2016.08); *A61K 9/0095* (2013.01); *A61K 31/198* (2013.01); *A61K 31/353* (2013.01); *A61K 31/736* (2013.01); *A23F 3/32* (2013.01); *A23L 2/39* (2013.01); *A23L 2/60* (2013.01); *A23L 27/30* (2016.08); *A23L 27/33* (2016.08); *A23L 27/37* (2016.08); *A23L 33/21* (2016.08); *A23V 2002/00* (2013.01)

(58) Field of Classification Search
None
See application file for complete search history.

(56) References Cited

U.S. PATENT DOCUMENTS

| | | |
|---|---|---|
| 7,815,960 B2 | 10/2010 | Quan et al. |
| 2003/0064104 A1* | 4/2003 | Stillman .................. A23L 2/38 424/490 |
| 2005/0003068 A1 | 1/2005 | Kester et al. |
| 2005/0090511 A1* | 4/2005 | Shibahara .............. A61K 45/06 514/263.31 |
| 2012/0225100 A1 | 9/2012 | Darcy et al. |
| 2012/0329736 A1* | 12/2012 | Huang ............... A61K 31/7024 514/25 |
| 2013/0115359 A1 | 5/2013 | Savant et al. |
| 2014/0322389 A1 | 10/2014 | Prakash et al. |
| 2015/0182579 A1* | 7/2015 | Hageman ............. A61K 31/716 424/750 |

OTHER PUBLICATIONS

Slavin et al., Partially Hydrolyzed Guar Gum: Clinical Nutrition Uses, 2003, Nutrition, 19: 549-552.*
"EstomaCalm," 2015, Estocalm, pp. 1-4, p. 2 para[1]; p. 2, para [2]; p. 3, para [1]; p. 3, para [2], p. 4, para [1]; p. 4, para [2]; p. 2, "Supplemental Facts."
"Sunphenon", Apr. 8, 2016, Taiyo International, pp. 1-2, p. 1, para [2].
International Search Report and Written Opinion issued in related International Patent Application No. PCT/US2018/027092, dated Jul. 3, 2018.
Yoon et al., "Chemical and Physical Properties, Safety and Application of Partially Hydrolized Guar Gum as Dietary Fiber," *J. Clin. Biochem. Nutr.*, vol. 42, No. 1, pp. 1-7 (2008).

* cited by examiner

*Primary Examiner* — Terry A McKelvey
*Assistant Examiner* — Catheryne Chen
(74) *Attorney, Agent, or Firm* — Foley & Lardner LLP

(57) ABSTRACT

Some embodiments comprise dietary supplements for treating or preventing traveler's diarrhea comprising: (a) about 1000 mg green tea extract comprising at least 90% (w/w) catechins; (b) about 4 g partially hydrolyzed guar gum (PHGG); (c) about 100 mg L-theanine; and (d) about 5 g non-sugar sweetener, wherein the sweetener does not contain a polyol. Some embodiments comprise dietary supplement for treating or preventing traveler's diarrhea comprising: (a) from about 250 mg to about 1,500 mg green tea extract comprising at least 90% (w/w) catechins; (b) from about 1 g to about 8 g partially hydrolyzed guar gum (PHGG); and (c) from about 15 mg to about 250 mg L-theanine. Some embodiments comprise methods for treating or preventing traveler's diarrhea, the method comprising: administering to a subject in need therefore a dietary supplement comprising (a) from about 250 mg to about 1,500 mg green tea extract comprising at least 90% (w/w) catechins; (b) from about 1 g to about 8 g partially hydrolyzed guar gum (PHGG); and (c) from about 15 mg to about 250 mg L-theanine.

14 Claims, No Drawings

COMPOSITIONS AND METHODS FOR TREATING TRAVELER'S DIARRHEA

FIELD OF THE INVENTION

This invention relates to dietary supplements and methods for treating and/or preventing traveler's diarrhea (TD).

BACKGROUND

Traveler's Diarrhea (TD) is believed to be caused by microorganisms such as bacteria and/or virus. TD can be associated with dietary changes that occur during international travels, or associated with consuming fresh, raw, and/or undercooked foods. TD can occur in more than 50% of individuals traveling to "high risk" regions of the world (e.g., tropical or semitropical areas, Latin America, the Caribbean, Southern Asia, Africa), resulting in up to 40 million cases of TD per year.

TD is commonly treated with antibiotics, though antibiotics can be associated with adverse side effects and are not effective for treating TD in all subjects.

There remains a need for improved therapeutic and preventative compositions and methods for TD.

SUMMARY

Surprisingly, the present inventor discovered dietary supplements and methods that solve the problems associated with prior therapeutic and preventative compositions for TD.

Provided are dietary supplements for treating or preventing traveler's diarrhea comprising: about 1000 mg green tea extract comprising at least 90% (w/w) catechins; about 4 g partially hydrolyzed guar gum (PHGG); about 100 mg L-theanine; and about 5 g non-sugar sweetener, wherein the sweetener does not contain a polyol.

In some embodiments, the dietary supplements further comprise a flavoring agent, such as a fruit juice flavor. In some embodiments the fruit juice flavor is lemon juice flavor, grapefruit juice flavor, cranberry juice flavor, or combinations thereof.

In some embodiments, the non-sugar sweetener is one or more of trehalose, sucralose, and acesulfame potassium.

In some embodiments, the PHGG has an average molecular size of about 20,000 Da. In some embodiments, the PHGG is in the form of a powder.

In some embodiments, the catechins comprise polyphenols comprising flavan-3-ol monomers. In some embodiments, the catechins comprise one or more of catechin gallate (CG), gallocatechin (GC), gallocatechin gallate (GCG), epicatechin (EC), epicatechin gallate (ECG), epigallocatechin (EGC), and epigallocatechin gallate (EGCG).

In some embodiments, the dietary supplement is in powder or liquid form. In some embodiments, the dietary supplement is in the form of a tablet.

In some embodiments, the dietary supplements are for treating or preventing traveler's diarrhea and comprise (a) from about 250 mg to about 1,500 mg green tea extract comprising at least 90% (w/w) catechins; (b) from about 1 g to about 8 g partially hydrolyzed guar gum (PHGG); and (c) from about 15 mg to about 250 mg L-theanine.

Also provided are methods for treating or preventing traveler's diarrhea, the method comprising: administering to a subject in need therefore a dietary supplement comprising (a) from about 250 mg to about 1,500 mg green tea extract comprising at least 90% (w/w) catechins; (b) from about 1 g to about 8 g partially hydrolyzed guar gum (PHGG); and (c) from about 15 mg to about 250 mg L-theanine.

In some embodiments, the methods further comprise mixing the dietary supplement with a liquid formulation prior to administration. In some embodiments, the liquid formulation comprises from about 250 mL to about 1 liter of a liquid. In some embodiments, the liquid is water or juice.

In some embodiments, the administering is via ingestion of the dietary supplement.

In some embodiments, the method comprises administering the dietary supplement from one to three times per day.

Some embodiments for treating or preventing traveler's diarrhea comprise methods wherein the dietary supplement comprises (a) about 1000 mg green tea extract comprising at least 90% (w/w) catechins; (b) about 4 g partially hydrolyzed guar gum (PHGG); (c) about 100 mg L-theanine; and (d) about 5 g of sweetener, wherein the sweetener does not contain a polyol. In some embodiments, the non-sugar sweetener is one or more of trehalose, sucralose, and acesulfame potassium. In some embodiments, the dietary supplement is in powder or liquid form.

DETAILED DESCRIPTION

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

The term "about" means that the number comprehended is not limited to the exact number set forth herein, and is intended to refer to numbers substantially around the recited number while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, "subject" denotes a human subject, which can be a male subject or a female subject. The age of the subject is not particularly limited; thus, the subject can be a child (e.g., 0-12 years of age), an adolescent (e.g., 13-17 years of age), or an adult (e.g., 18 years of age or older).

"Traveler's Diarrhea" is a temporary condition characterized by the passage of at least three unformed stools in a 24-hour period, along with at least one symptom selected from nausea, vomiting, abdominal cramps or pain, fever, blood in the stool. Additional symptoms of TD can include fatigue, loss of appetite, flatulence, and general discomfort. Without being bound by theory, it is believed that TD is often caused by infection with bacteria, protozoa, or viruses ingested by consuming food or water that has been contaminated.

"Treatment" and "prevention" are to be considered in their broadest context. The term in "treatment" does not necessarily imply that the subject is treated until total recovery. Similarly, "prevention" does not necessarily mean that the subject will not eventually contract a condition. Accordingly, treatment and prevention include amelioration of one or more symptoms of a particular condition or preventing or otherwise reducing the risk of development of a condition. The term "prevention" may be considered as reducing the severity or onset of a particular condition. "Treatment" may also reduce the severity of an existing condition.

The present invention relates to dietary supplements for treating or preventing TD comprising catechins and prebiotioc dietary fiber (e.g., a water-soluble dietary fiber).

Catechins

As used herein, the term "catechin" refers to a polyphenol in the chemical family of flavonoids. Without being bound by theory, it is believed that catechin can suppress microbial growth in the intestines believed to be associated with TD.

The catechin can be, but is not limited to, catachin monomers (e.g., flavan-3-ol monomers), catechin isomers, and combinations thereof. Some embodiments comprise catechin esters, such as catechin gallate (CG), gallocatechin (GC), gallocatechin gallate (GCG), epicatechin (EC), epicatechin gallate (ECG), epigallocatechin (EGC), and epigallocatechin gallate (EGCG), and combinations of two or more thereof.

Catechins can be derived from a variety of sources, such as tea plants (e.g., Camellia sinensis), cocoas (e.g., made from seeds of Theobroma cacao), and chocolates. In some embodiments, the catechins are extracted from a plant, such as a green tea plant (e.g., Camellia sinensis).

Some embodiments comprise a plant extract that comprises catechins. In some embodiments, the plant extract comprises more than about 70% (w/w) catechins, more than about 80% (w/w) catechins, more than about 90% (w/w) catechins, or more than about 95% (w/w) catechins. In some embodiments, the plant extract comprises more than 70% (w/w) catechins, more than 80% (w/w) catechins, more than 90% (w/w) catechins, or more than 95% (w/w) catechins.

In some embodiments, the plant extract is a green tea extract. The extract can be of any suitable green tea variety, such as sencha, fukushami sencha, gyokuro, kabusecha, matcha, tencha, genmaicha, hojicha, shincha, ichibancha, nibancha, or sanbancha.

Prebiotic Dietary Fiber

As used herein, "prebiotic dietary fiber" refers to a water-soluble fiber derived from galactomannan. In some embodiments, the prebiotic dietary fiber is formed by partially hydrolyzing galactomannan, e.g., with a β-endo-mannanase enzyme. Without being bound by theory, it is believed that endo-β-D-mannanase can hydrolyze galactomannan by selectively cutting the main mannan backbone-chain, leaving the pendant galactosyl groups intact. In some embodiments, the prebiotic dietary fiber is partially hydrolyzed galactomannan from gum guar, coffee beans, soy beans, alfalfa seeds, pineapple, sugar beets, and/or locust beans. In particular embodiments, the galactomannan is from gum guar, which can be obtained, e.g., by grinding the endosperm portion of a Cyamoposis tetragonolobus L. plant.

Some embodiments comprise partially hydrolyzed gum, such as partially hydrolyzed guar gum (PHGG). Physical and chemical properties of PHGG are described in Yoon et al., "Chemical and Physical Properties, Safety and Application of Partially Hydrolized Guar Gum as Dietary Fiber," J. Clin. Biochem. Nutr., 42(1): 1-7 (2008), which is incorporated herein in its entirety. An exemplary PHGG is sold under the tradename SUNFIBER® (commercially available from Taiyo Kagaku in Japan).

In some embodiments, the partially hydrolyzed gum (e.g., PHGG) has a molecular size ranging from 1,000 Da to 100,000 Da. In some embodiments, the partially hydrolyzed gum (e.g., PHGG) has the same chemical structure as the gum (e.g., guar gum), but with a molecular weight of about 10% or less of the gum.

In some embodiments, the prebiotic dietary fiber is not inulin (e.g., the composition is free of or substantially free of inulin). In some embodiments, the prebiotic dietary fiber is not a fructooligosaccharide (FOS) (e.g., the composition is free of or substantially free of fructooligosaccharide). In some embodiments, the prebiotic dietary fiber is not a isomaltooligosaccharide (IMO) (e.g., the composition is free of or substantially free of isomaltooligosaccharide).

Additional Ingredients

In some embodiments, the compositions further comprising additional ingredients such as a sweetener, a flavoring agent, L-theanine, and/or a probiotic.

A sweetener is an additive intended to provide a sweet taste, and can be a natural sweetener or an artificial sweetener. Exemplary sweeteners include trehalose, sucralose, acesulfame potassium, Aspartame, Cyclamate, Saccharin, Neotame, Stevia (steviol glycosides, including Reb. A), Monk Fruit, Fructose, Allulose, Palatinose, and combinations of two or more thereof.

In some embodiments, the sweetener does not serve as a sufficient carbon source to support growth of living cells such as microorganisms. In some embodiments, the sweetener is not glucose (e.g., the dietary supplement includes no or substantially no glucose). In some embodiments, the sweetener is not sucrose (e.g., the dietary supplement includes no or substantially no sucrose). In some embodiments, the sweetener is not a polyol (e.g., the dietary supplement includes no or substantially no polyols). Exemplary polyols include xylitol, erythritol, sorbitol, and maltitol.

A flavoring agent is an additive intended to provide flavor to the composition. Flavoring agents include fruit juice flavors or other natural flavored agents. In some embodiments, the flavoring agent comprises lemon flavoring, grapefruit flavoring, cranberry flavoring, raspberry flavoring, or combinations thereof.

Some embodiments comprise L-theanine, which can be prepared from an enzyme-catalyzed reaction involving glutamine and ethylamine. In some embodiments, the L-theanine is purified L-theanine or substantially pure L-theanine. L-theanine can be purchased under the tradename SUNTHEANINE® from Taiyo Kagaku in Japan.

Some embodiments comprise vitamin C. Some embodiments comprise citric acid, tapioca maltodextrin, natural flavors, and/or natural colors.

Some embodiments comprise a probiotic. In some embodiments, the probiotic is one or more probiotic bacterial strain (which can be available in dry form (such as spores) and retain viability in said form for several months) or an enzyme produced by the probiotic bacterial strain. Exemplary probiotics include Bacillus coagulans bacterial strains, Lactobacillus bacterial strains, and combinations thereof. In other embodiments, the dietary supplement does not include a probiotic (e.g., the dietary supplement is free of or substantially free of a probiotic).

In some embodiments, the dietary supplement does not include genetically modified organisms, gluten, wheat, dairy products, yeast, nuts, soy, sugar (e.g., glucose), salt (e.g., sodium chloride), animal derivatives, magnesium stearate, artificial color, and/or preservatives (e.g., the dietary supplement is free of or substantially free of genetically modified organisms, gluten, wheat, dairy products, yeast, nuts, soy, sugar (e.g., glucose), salt (e.g., sodium chloride), animal derivatives, magnesium stearate, artificial color, and/or preservatives).

In some embodiments, all ingredients in the dietary supplement are food-grade (GRAS) and safe for consumption.

Treatment/Prevention Methods

Some embodiments involve treating or preventing TD by orally administering dietary supplements to a subject in need thereof.

In some embodiments, the subject is a child. In other embodiments, the subject is an adolescent. In still other embodiments, the subject is an adult. In some embodiments, the subject is from 0 to about 12 years of age, such as 1, 2, 3, 4, 5, 6, 7, 8, 9, 10, 11, or 12 years of age. In some embodiments, the subject is from about 13 to about 17 years of age, such as 13, 14, 15, 16, or 17 years of age. In some embodiments, the subject is about 18 years of age or older, such as 18, 19, 20, 21, 22, 23, 24, 25, 26, 27, 28, 29, or 30 years of age. In some embodiments, the subject is older than 30 years of age.

The dietary supplement can be in any form suitable form. For example, the supplement can be formulated in a powder, a liquid, a solid, a tablet (e.g., an effervescent or chewable tablet), a sachet, a capsule, a stick pack, a gel, a solution, or a syrup. The dietary supplement can be formulated in any suitable amount, such as about 1 g, about 2 g, about 3 g, about 4 g, about 5 g, or more than about 5 g of the dietary supplement.

In some embodiments, the dietary supplemented is formulated for direct consumption. In other embodiments, the dietary supplement is formulated to be mixed with a liquid (e.g., water, juice, or any other potable liquid) or other food product prior to being consumed. For instance, the dietary supplement can be mixed with from about 250 ml to about 1 liter of a liquid, such as about 250 ml, about 300 ml, about 500 ml, about 750 ml, or about 1000 ml of a liquid. In some embodiments, the dietary supplement is mixed with 250 ml to about 1 liter of a liquid, such as 250 ml, 300 ml, 500 ml, 750 ml, or 1000 ml of a liquid.

Some embodiments comprise administering an effective amount of the dietary supplement to treat or prevent TD. In some embodiments, the effective amount is provided by administering a single daily dose of the dietary supplement. Some embodiments comprise administering a dietary supplement more than once per day, such as twice per day or three times per day.

In some embodiments, the dietary supplement comprises at least about 250 mg, at least about 500 mg, at least about 750 mg, at least about 1000 mg, at least about 1250 mg, or at least about 1500 mg of plant extract (e.g., plant extract comprising at least 90% catechins). In some embodiments, the dietary supplement comprises at least 250 mg, at least 500 mg, at least 750 mg, at least 1000 mg, at least 1250 mg, or at least 1500 mg of plant extract. Some embodiments comprise from about 250 mg to about 1500 mg of plant extract, such as about 500 mg to about 1000 mg of plant extract. Some embodiments comprise from 250 mg to 1500 mg of plant extract, such as 500 mg to 1000 mg of plant extract. Some embodiments, comprise about 250 mg, about 500 mg, about 750 mg, about 100 mg, or about 1250 mg of plant extract. Some embodiments, comprise 250 mg, 500 mg, 750 mg, 100 mg, or 1250 mg of plant extract.

In some embodiments the dietary supplement comprises at least about 1 gram of prebiotic dietary fiber (e.g., PHGG), such as about 2 g, about 3 g, about 4 g, about 5 g, about 6 g, about 7 g, or about 8 g of prebiotic dietary fiber. In some embodiments the dietary supplement comprises at least 1 gram of prebiotic dietary fiber, such as 2 g, 3 g, 4 g, 5 g, 6 g, 7 g, or 8 g of prebiotic dietary fiber. Some embodiments comprise about 1 g to about 8 g of prebiotic dietary fiber, such as about 2 g to about 7 g, or about 3 g to about 6 g, or about 2 g to about 5 g of dietary fiber. Some embodiments comprise 1 g to 8 g of prebiotic dietary fiber, such as 2 g to 7 g, or 3 g to 6 g, or 2 g to 5 g of dietary fiber.

In some embodiments, the dietary supplement comprises at least about 15 mg of L-theanine, such as at least about 50 mg, at least about 100 mg, at least about 150 mg, at least about 200 mg, or at least about 250 mg of L-theanine. In some embodiments, the dietary fiber comprises at least 15 mg of L-theanine, such as at least 50 mg, at least 100 mg, at least 150 mg, at least 200 mg, or at least 250 mg of L-theanine. Some embodiments comprise about 15 mg, about 50 mg, about 100 mg, about 150 mg, about 200 mg, or about 250 mg L-theanine. Some embodiments comprise 15 mg, 50 mg, 100 mg, 150 mg, 200 mg, or 250 mg L-theanine.

In some embodiments, the dietary supplement comprises at least about 500 mg vitamin C, such as at least about 750 mg, at least about 1000 mg, at least about 1250, at least about 1500, or at least about 2000 mg of vitamin C. In some embodiments, the dietary supplement comprises at least 500 mg vitamin C, such as at least 750 mg, at least 1000 mg, at least 1250, at least 1500, or at least 2000 mg of vitamin C. In some embodiments, the dietary supplement comprises about 500 mg, about 750 mg, about 1000 mg, about 1250, about 1500, or about 2000 mg of vitamin C. In some embodiments, the dietary supplement comprises 500 mg, 750 mg, 1000 mg, 1250, 1500, or 2000 mg of vitamin C.

EXAMPLES

The below examples are not intended to be limiting of the scope of the present invention Example 1: Dietary Supplement Formulation 1

Dietary supplements were prepared using the following materials:
Lemonade Flavor
1000 mg Green Tea Extract (>90% catechins);
4 g PHGG (SUNFIBER®);
100 mg L-theanine (SUNTHEANINE®);
5 g non-sugar sweetener blend (trehalose and sucralose);
5 mg lemon juice flavor
1000 mg Vitamin C
2.5 g Citric acid
2.4 g Tapioca maltodextrin
Cranberry-Raspberry Flavor A dietary supplement was prepared using the above formula, but with 1.85 g of tapioca maltodextrin and 5 mg cranberry juice flavor instead of lemon juice flavor. The supplement also included 0.125 g of a natural color derived from fruits and vegetables.
Grapefruit Flavor A dietary supplement was prepared using the above "Lemonade" flavor formula, but with 0.485 g tapioca maltodextrin and 5 mg grapefruit juice flavor instead of lemon juice flavor. The supplement also included 0.05 g of a natural color derived from fruits and vegetables.

Example 2: Dietary Supplement Formulation 2

A dietary supplement is prepared using the following materials:
1000 mg Green Tea Extract (>90% catechins);
4 g PHGG (SUNFIBER®);
100 mg L-theanine (SUNTHEANINE®);
5 g non-sugar sweetener blend (trehalose and sucralose);
5 mg lemon juice flavor The dietary supplement is mixed with 500 mL water in a bottle, and shaken until the dietary supplement is dissolved. The contents are then consumed as needed.

Example 3: A Method for Providing a Dietary Supplement to Promote Digestive Health A person desiring to prevent or limit the symptoms of TD (e.g., loose stools, nausea, vomiting, abdominal cramps or pain, fever, blood in the stool, fatigue, loss of appetite, flatulence, and/or general discomfort) mixes the dietary supplement into a bottle of drinking water, and shakes the bottle until the dietary supplement dissolves. The person then consumes the bottle of drinking water as needed. Additional bottles can be prepared and consumed as needed.

What is claimed is:

1. A method for treating or preventing traveler's diarrhea, the method comprising administering to a subject in need thereof a dietary supplement consisting essentially of:
   (a) from about 250 mg to about 1,500 mg of green tea extract comprising at least 90% (w/w) catechins;
   (b) from about 1 g to about 8 g partially of hydrolyzed guar gum (PHGG);
   (c) from about 15 mg to about 250 mg of L-theanine; and
   (d) a sweetener that does not contain a polyol; and
   wherein the traveler's diarrhea is caused by ingesting pathogenic bacteria, viruses, and/or protozoa, and wherein the dietary supplement is substantially free from bacteria and inulin.

2. The method of claim 1, further comprising mixing the dietary supplement with a liquid formulation prior to administration.

3. The method of claim 2, wherein the liquid formulation comprises from about 250 mL to about 1 liter of a liquid.

4. The method of claim 3, wherein the liquid is water or juice.

5. The method of claim 1, wherein the administering is via ingestion of the dietary supplement.

6. The method of claim 1, wherein the method comprises administering the dietary supplement from one to three times per day.

7. The method of claim 1, wherein the dietary supplement consists essentially of:
   (a) about 1000 mg of the green tea extract comprising at least 90% (w/w) catechins;
   (b) about 4 g of the partially hydrolyzed guar gum (PHGG);
   (c) about 100 mg of the L-theanine; and
   (d) about 5 g of the sweetener.

8. The method of claim 7, wherein the sweetener is one or more of trehalose, sucralose, and acesulfame potassium.

9. The method of claim 1, wherein the dietary supplement is in powder or liquid form.

10. The method of claim 1, wherein the green tea extract comprises at least 95% (w/w) catechins.

11. A method for treating or preventing traveler's diarrhea, the method comprising administering to a subject in need thereof a dietary supplement consisting essentially of:
    (a) from about 250 mg to about 1,500 mg of green tea extract comprising at least 90% (w/w) catechins;
    (b) from about 1 g to about 8 g of partially hydrolyzed guar gum (PHGG);
    (c) from about 15 mg to about 250 mg of L-theanine;
    (d) a sweetener that does not contain a polyol; and
    (e) a flavoring agent; and
    wherein the traveler's diarrhea is caused by ingesting pathogenic bacteria, viruses, and/or A protozoa, and wherein the dietary supplement is substantially free from bacteria and inulin.

12. The method of claim 11, wherein the flavoring agent is a fruit juice flavor, vitamin C, citric acid, or combinations thereof.

13. The method of claim 12, wherein the fruit juice flavor is lemon juice flavor, grapefruit juice flavor, cranberry juice flavor, or combinations thereof.

14. A method for treating or preventing traveler's diarrhea, the method comprising administering to a subject in need thereof a dietary supplement consisting essentially of:
    (a) from about 250 mg to about 1,500 mg of green tea extract comprising at least 90% (w/w) catechins;
    (b) from about 1 g to about 8 g of partially hydrolyzed guar gum (PHGG);
    (c) from about 15 mg to about 250 mg of L-theanine;
    (d) a sweetener that does not contain a polyol;
    (e) a flavoring agent; and
    (f) one or more probiotic bacterial strains; and
    wherein the traveler's diarrhea is caused by ingesting pathogenic bacteria, viruses, and/or protozoa, and wherein the dietary supplement is substantially free from inulin.

* * * * *